United States Patent [19]

Smith, III et al.

[11] Patent Number: 5,621,108
[45] Date of Patent: Apr. 15, 1997

[54] PROCESSES AND INTERMEDIATES FOR PREPARING MACROCYCLES

[75] Inventors: Amos B. Smith, III, Merion; Stephen M. Condon; Johnnie L. Leazer, Jr., both of Philadelphia; Robert E. Maleczka, Media; John A. McCauley, Philadelphia, all of Pa.; James W. Leahy, San Leandro, Calif.

[73] Assignee: Trustees of the University of Pennsylvania, Philadelphia, Pa.

[21] Appl. No.: 349,413

[22] Filed: Dec. 5, 1994

[51] Int. Cl.$^6$ .................................................. C07D 405/06
[52] U.S. Cl. ............................................ 546/207; 549/20
[58] Field of Search .................................................. 546/207

[56] References Cited

U.S. PATENT DOCUMENTS 5,164,399  11/1992  Failli et al. ............................... 514/296
5,252,579  10/1993  Skotnicki et al. ....................... 514/291

OTHER PUBLICATIONS

Crisp, G. and Glink, "Elaboration of the Side Chain of α–Amino Acids Containing a Vinyl Iodide by Palladium–Catalysed Coupling", *Tetrahedron* 1994, 50(8), 2623–2640.
Eshelman, J. et al., "Diastereoselective [2,3] Wittig Rearrangement of Carbohydrate–derived Tertiary Allylic Ethers. 1. Synthesis of the $C^{11}$–$D^{18}$ Subunit of Herbimycin A From D–Glucose", *Tetrahedron Letters* 1993, 34(5), 749–752.
Goulet, M.T. and Boger, "Degradative Studies on the Tricarbonyl Containing Macrolide Rapamycin", *Tetrahedron Letters* 1990, 31(34), 4845–4848 and Corrigendum *Tetrahedron Letters* 1991, 32, 6454.
Condon, S. et al., "Studies Directed Towards the Total Synthesis of Rapamycin: Construction of a C29–C39 Fragment", Thirty–Third National Organic Chemistry Symposium Program and Abstracts, Jun. 13–17, 1993, Montana State University, Bozeman, Montana.
Smith III, A. et al., "Rapamycin and Demethoxyrapamycin: Synthetic Studies", American Chemical Society, Division of Organic Chemistry, 207th ACS National Meeting, Mar. 13–17, 1994, San Diego, CA.
Smith III, A. et al, "The Total Syntheses of Rapamycin and Demethoxyrapamycin", American Chemical Society, Division of Organic Chemistry, 209th ACS National Meeting, Apr. 206, 1995, Anaheim, CA.
Teague et al. "Synthesis and study of a non macrocyclic FK506 derivative" CA 121:255492 (1994).
Batchelor, M.J. et al., "A Novel Application of the Dess–Martin Reagent to the Synthesis of an FK506 Analogue and Other Tricarbonyl Compounds", *Tetrahedron* 34, 167–170 (1993).
Chen, S. et al., "Application of the Ibuka–Yamamoto Reaction to a Problem in Stereochemical Communication: A Strategy for the Stereospecific Synthesis and Stabilization of the Triene Substructure of Rapamycin Through Sulfone Substitution", *J. Org. Chem.* 1991, 56, 5834–5845.

Corey, E.J. and Fuchs, "A Synthetic Method for Formyl–Ethynyl Conversion (RCHO–RC=CH or RC=$CR^1$)", *Tetrahedron Letters* 1972, 13, 3769–3772.
Crisp, G. et al., "Synthesis and Transformation of Trialkylstannyl–Substituted Allylglicine Derivatives", *Tetrahedron Letters* 1992, 33(32), 4649–4652.
Dess, D.B. et al., "Readily Accessible 12–I–$5^1$ Oxidant for the Conversion of Primary and Secondary Alcohols to Aldehydes and Ketones", *J. Org. Chem.* 1983, 48, 4155–4156.
Fisher, M. et al., "Synthetic Studies Toward Rapamycin: A Solution to a Problem in Chirality Merger Through Use of the Ireland Reaction", *J. Org. Chem.* 1991, 56, 5826–5834.
Greene, T.W. and Wuts, *Protective Groups in Organic Synthesis*, 2d Ed., Wiley & Sons, 1991.
Hayward, C. et al., "An Application of the Suarez Reaction to the Regiospecific and Stereospecific Synthesis of the $C_{28}$–$D_{42}$ Segment of Rapamycin", *Tetrahedron Letters* 1993, 34(25), 3989–3992.
Hayward, C. et al., "Total Synthesis of Rapamycin vi a Novel Titanium–Mediated Aldol Macrocyclization Reaction", *J. Am. Chem. Soc.* 1993, 115, 9345–9346.
Horvath, R. et al., "An Applicaiton of the Evans–Prasad 1,3–Syn Diol Synthesis to a Stereospecific Synthesis of the $C_{10}$–$C_{27}$ Segment of Rapamycin", *Tetrahedron Letters* 1993, 34(25), 3993–3996.
March, J. *Advanced Organic Chemistry*, Fourth Ed., Wiley & Sons, New York, 1992, p. 1194.
Meyer, S. et al., "Synthetic Investigations of Rapamycin. I. Synthesis of a $C_{10}$–$C_{21}$ Fragment", *J. Org. Chem.* 1992, 57, 5058–5060.
Nicolaou, et al., "Stereocontrolled Total Synthesis of Lipoxins B", *Synthesis* 1986, 453–461.
Nicolaou, K. et al., "Total Synthesis of Rapamycin", *J. Am. Chem. Soc.* 1993, 115, 4419–4420.
Nicolaou, K. et al., "Stereoselective Construction of the $C^{21}$–$C^{42}$ Fragment of Rapamycin", *J. Chem. Soc., Chem. Commun.* 1993, 619–622.
Piscopio, A.D. et al., "A Highly Convergent Strategy Towards Rapamycin. Stereoselective Construciton of the $C^8$–$C^{18}$ Fragment", *J. Chem. Soc., Chem. Commun.* 1993, 617–618.
Romo, D. et al., "Synthetic Investigations of Rapamycin. 2. Synthesis of a $C_{22}$–$C_{42}$ Fragment", *J. Org. Chem.* 1992, 57, 5060–5063.
Romo, D. et al., "Total Synthesis of (–)–Rapamycin Using an Evans–Rischchenko Fragment Coupling", *J. Am. Chem. Soc.* 1993, 115, 7906–7907.

(List continued on next page.)

Primary Examiner—Ceila Chang
Attorney, Agent, or Firm—Woodcock Washburn Kurtz Mackiewicz & Norris

[57] ABSTRACT

Novel processes for the preparation of lactam- and lactone-containing macrocyles are provided. In preferred embodiments, rapamycin and demethoxyrapamycin are prepared by a convergent synthesis regime. Intermediates useful in the synthetic processes are also provided.

10 Claims, 10 Drawing Sheets

OTHER PUBLICATIONS

Smith, A.B. et al., "Rapamycin Synthetic Studies. 1. Construction of the C(27)–C(24) Subunit", *Tetrahedron Letters* 1994, 35(28), 4907–4910.

Smith, A.B. et al., "Rapamycin Synthetic Studies. 2. Elaboration of the C(10)–C(26) Perimeter", *Tetrahedron Letters* 1994, 35(28), 4911–4914.

Yohannes, D. and Danishefsky, "Degradation of Rapamycin: Retrieval of Major Intact Subunits", *Tetrahedron Letters* 1992, 33(49), 7469–7472.

Yohannes, D. et al., "Degradation of Rapamycin: Synthesis of a Rapamycin Derived Fragment Contianing the Tricarbonyl and Triene Sectors", *Tetrahedron Letters* 1993, 34(13), 2075–2078.

Zhang, H. et al., "Palladium– and Molybdenum–Catalyzed Hydrostannation of Alkynes. A Novel Access to Regio– and Stereodefined Vinylstannanes", *J. Org. Chem.* 1990, 55, 1857–1867.

Anderson, J.C. et al., "Studies towards the total synthesis of rapamycin: a convergent and stereoselective synthesis of the $C_{22}$–$C_{32}$ carbon framework", *Tetrahedron Letters* 1994, 35(13), 2087–2090.

Crisp, G.T. and Glink, P.T., "Elaboration of the side chain of α–Amino acids by palladium–catalysed stille couplings", *Tetrahedron Letters* 1994, 50(10), 3213–3234.

Boden, E. and Keck, "Proton–Transfer Steps in Steglich Esterification: A Very Practical new Method for Macrolactonization", *J. Org. Chem.* 1985, 50, 2394–2395.

Farina, V. and Krishman, B., "Large rate accelerations in the stille reaction with tri–2–furylphosphine and triphenylarsine as palladium ligands: mechanistic and synthetic implications", *J. Am. Chem. Soc.* 1991, 113, 9585–9595.

Férézou, J.P. et al., "Model studies of palladium–catalysed coupling reactions for the South–North attachment of avermectins", *Synlett* 1991, Jan., 53–56.

Hale, M.R., and Hoveyda, A.H., "Siloxanes: Versatile templates for acyclic stereocontrol. Synthesis of the C27–C33 segment of rapamycin", *J. Org. Chem.* 1992, 57, 1643–1645.

Kalivretenos, A. et al., "Synthesis of β–resorcyclic macrolides via organopalladium chemistry. Application to the total synthesis of (S)–searalenone", *J. Org. Chem.* 1991, 56, 2883–2894.

Kouklovsky, C. et al., "Studies towards the total synthesis of rapamycin: preparation of the cyclohexyl $C_{33}$–$C_{42}$ fragment and further coupling to afford the $C_{22}$–$C_{42}$ carbon unit", *Tetrahedron Letters* 1994, 35(13), 2091–2094.

Ley, S.V. et al., "Studies towards the total synthesis of rapamycin: preparation of the $C_{10}$–$C_{17}$ carbon unit", *Tetrahedron Letters* 1994, 35(13), 2095–2098.

Mc Murry, J.E. and Scott, W.J., "A method for the regiospecific of enol triflates by enolate trapping", *Tetrahedron Letters* 1983, 24(10), 979–982.

Mc Murry, J.E. and Scott, W.J., "A new method of olefin synthesis. coupling of lithium dialkulcuprates with enol triflates", *Tetrahedron Letters* 1980, 21, 4313–4316.

Reich, H.J. et al., "Solution Ion pair structure of 2–lithio–1, 3–dithianes in THF and THF–HMPA", *Tetrahedron Letters* 1994, 50(20), 5869–5880.

Sin, N. and Kallmerten, "Diastereoselective [2,3] wittig rearrangement of carbohydrate–derived tertiary allylic ethers. 2. Synthesis of an advanced rapamycin intermediate from d–glucose", *Tetrahedron Letters* 1993, 34(5), 753–756.

Stille, J.K. and Tanaka, M., "Intramolecular palladium–catalyzed cyclizations of esters containing vinyl triflate and vinylstannane groups at the termini: synthesis of large–ring lactones", *J. Am. Chem. Soc.* 1987, 109, 3785–3786.

Stille, J.K. and Groh, B.L., "Stereospecific cross–coupling of vinyl halides with vinyl tin reagents catalyzed by palladium", *J. Am. Chem. Soc.* 1987, 109, 813–817.

Zibuck, R. et al., "Total synthesis of (+)–latrunculin B", *J. Am. Chem. Soc.* 1986, 108, 2451–2453.

Boden et al. "Proton transfer steps in Steglich esterification:a very practical new method fo macrolactonization" J. Or. Chem. v. 50, pp. 2394–2395 1985.

Crisp et al. "Elaboration of the side chain of alpha amino acids by Palladium catalysed stille couplings" Tetrahedron v. 50(10) pp. 3213–3234 1994.

PROCESSES AND INTERMEDIATES FOR PREPARING MACROCYCLES

GOVERNMENT SUPPORT

Certain of the inventors were supported by National Institutes of Health Grant GM29028.

FIELD OF THE INVENTION

This invention relates to methods for the preparation of lactam- and lactone-containing macrocycles such as rapamycin and demethoxyrapamycin, and to intermediates useful in their preparation.

BACKGROUND OF THE INVENTION

Rapamycin and demethoxyrapamycin are two members of a growing class of macrolide natural products possessing marked immunosuppressive properties. Recently, several groups have focused on the preparation of both modest and advanced fragments of the polyketide skeleton, culminating in three total syntheses of rapamycin. In addition, several groups have prepared semi-synthetic analogs of rapamycin to improve upon its impressive therapeutic profile as well as to gain insight into the as-yet-unresolved mechanism of action.

To date, four research groups have reported the discovery and isolation of a 220 kDa protein which is thought to be the direct intracellular target of the rapamycin-FKBP complex. This protein shares structural homology with a number of known lipid kinases although its specific role in signal transduction and immunosuppression remains unclear. It has, however, been established that rapamycin interferes with a $Ca^{2+}$-independent signaling pathway emanating from the IL-2 receptor, thus prohibiting the progression of activated T cells from the G1 to the S phase of the cell cycle, perhaps via indirect inhibition of a cyclin dependent kinase specifically required for this transition.

There is a need for improved synthetic methods for the preparation of rapamycins. This invention is directed to this important end.

OBJECTS OF THE INVENTION

It is one object of the present invention to provide lactam- and/or lactone-containing macrocycles;

It is a further object to provide processes for the preparation of rapamycin, demethoxyrapamycin, and C-27 epirapamycin.

It is another object of this invention to provide intermediates useful in the processes.

SUMMARY OF THE INVENTION

These and other objects are satisfied by the present invention, which provides synthetic methods for the preparation of macrocycles, and novel compounds useful in the syntheses.

In certain embodiments, methods are provided for the preparation of a compound having formula (VII)

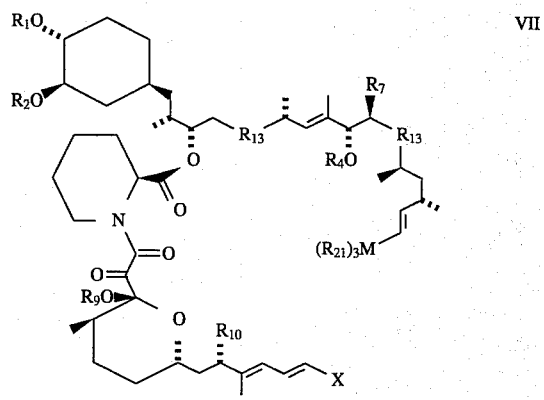

comprising the steps of:
providing a first compound of formula IV:

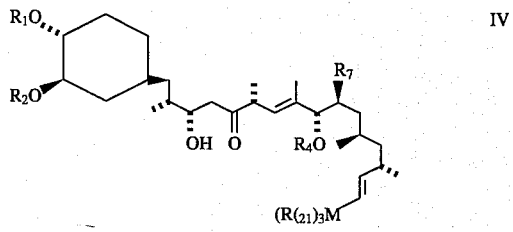

and contacting said compound with a compound of formula (VI):

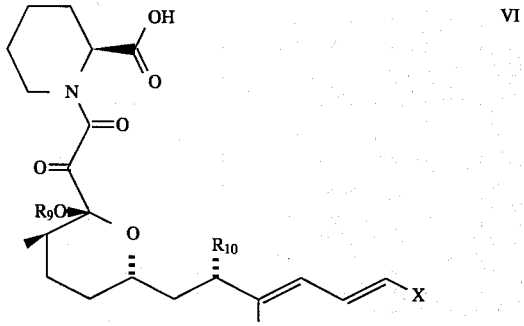

for a time and under reaction conditions effective to form said compound of formula VII;
wherein:
$R_1$, $R_4$, and $R_9$ are, independently, hydrogen or a hydroxyl protecting group;
$R_2$ is alkyl having one to about six carbons;
$R_7$ is hydrogen or alkoxy having one to about six carbons;
$R_{10}$ is H, OH, or alkoxy having one to about six carbons;
$R_{21}$ is alkyl having one to about six carbons;
M is a metal atom; and
X is halogen.
In preferred embodiments $R_7$ is H or methoxy, and M is Sn.
Preferably the hydroxyl protecting groups are selected from the group consisting of TIPS, PMBO, TESO and TBS. More preferably, $R_1$ is TIPS; $R_3$ is H; $R_4$ is TBS; and $R_9$ is TES.

Preferred embodiments further comprise treating said compound of formula VII for a time and under reaction conditions effective to form a compound of formula XV:

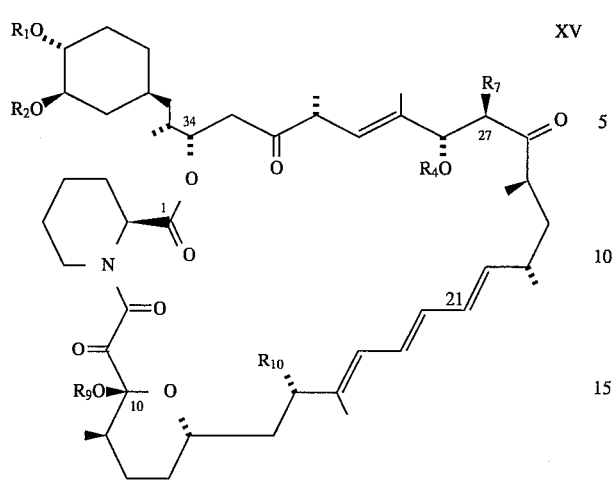

XV

Preferably, the protecting groups are then removed.

Also provided is a method for the preparation of a compound of formula IV:

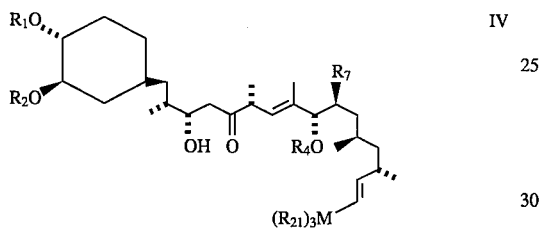

IV comprising the steps of:

providing a compound of formula II:

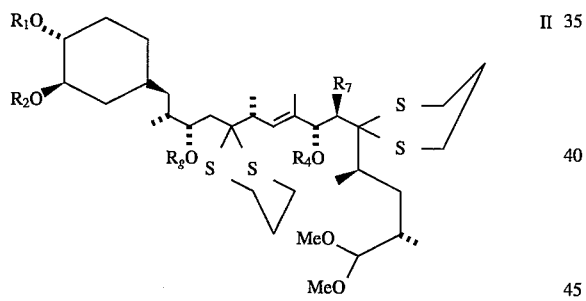

II treating said compound of formula II for a time and under conditions effective to form a terminal acetylene of formula III:

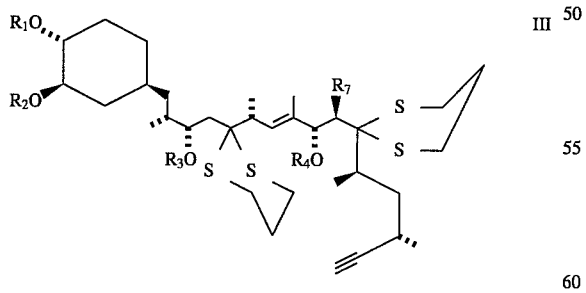

III and treating said terminal acetylene for a time and under conditions effective to form said compound of formula IV.

In some preferred embodiments said compound of formula II is formed by the reaction of an epoxide of formula V:

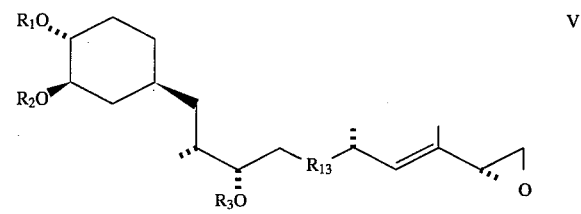

V and a reagent of formula XVI:

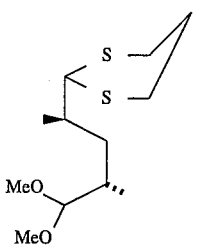

XVI

In other preferred embodiments said compound of formula II is formed by the reaction of an aldehyde of formula XIII:

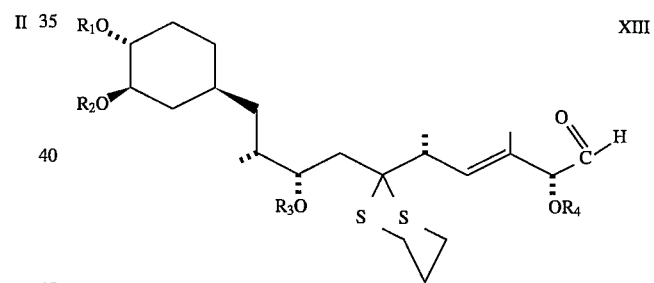

XIII and a reagent of formula XVI:

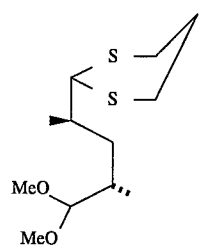

XVI

Also provided is a method for the preparation of a divinyl halide of formula VI:

comprising the steps of:
providing an orthoester of formula IX;

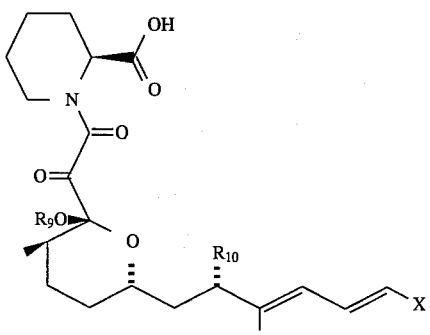

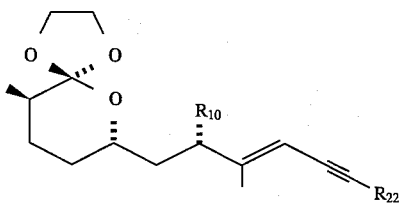

treating said orthoester for a time and under conditions effective to form an aldehyde of formula X;

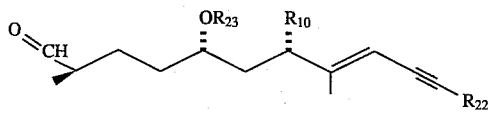

contacting said aldehyde with 2-carboxy-N-acetoylpiperidine for a time and under conditions effective to form a compound of formula XII;

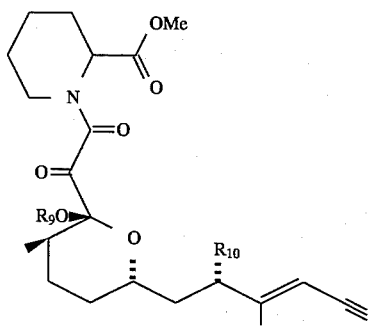

and treating said compound of formula XII for a time and under conditions effective to form said divinyl halide of formula VI.

Also provided according to the invention are novel intermediates, useful in the methods of the invention, having formula I:

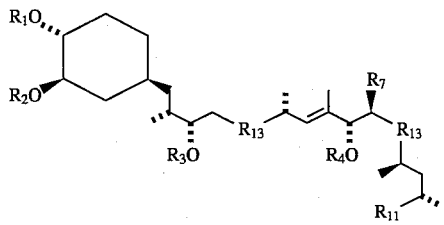

wherein:

$R_1$, $R_3$ and $R_4$ are independently H or a hydroxyl protecting group;

$R_2$ is alkyl having from one to six carbons;

$R_7$ is H or alkoxy;

$R_{13}$ is carbonyl group or protected derivative thereof;

$R_{11}$ has the formula —CH(OCH$_3$)$_2$, —C≡C—R$_{12}$ or cis-CH=CH-M(nC$_4$H$_9$)$_3$;

wherein:

$R_{12}$ is H or trimethylsilyl; and

M is a metal atom.

In certain preferred embodiments $R_7$ is H, and in other preferred embodiments $R_7$ is methoxy.

Preferably, $R_{11}$ has the formula —CH(OCH$_3$)$_2$, —C≡C—R$_{12}$ or cis-CH=CH-M(nC$_4$H$_9$)$_3$; and M is Sn.

The compound of claim 6 wherein $R_3$ is H. In certain preferred embodiments $R_{11}$ is —CH(OCH$_3$)$_2$ or —C≡C—R$_{12}$, and said protected derivative of said carbonyl group of said group $R_{13}$ is a 1,3-dithiane.

Preferably, $R_2$ is methyl; and said hydroxyl protecting groups are selected from the group consisting of TIPS, PMBO, TES and TBS. In particularly preferred embodiments $R_1$ is TIPS, $R_3$ is PMB and $R_4$ is TBS.

Also provided are compounds of formula V:

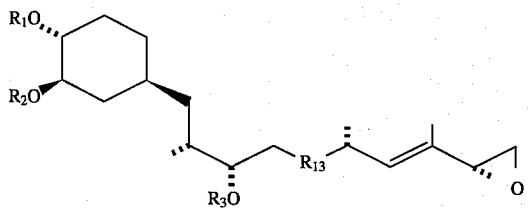

wherein $R_1$, $R_2$, $R_3$ and are as defined above.

Compound are also provided having formula VI:

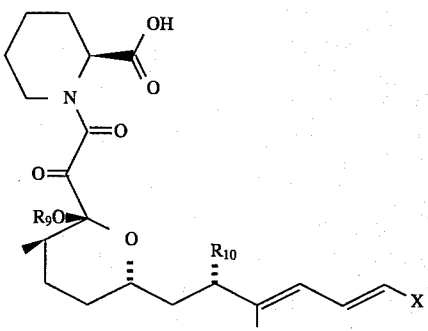

wherein:

$R_9$ is H or a hydroxyl protecting group;

$R_{10}$ is H, OH or alkoxy having one to about six carbon atoms; and

X is halogen, preferably iodine.

In certain embodiments $R_8$ is H, and $R_{10}$ is methoxy.

Also provided are compounds having formula VII:

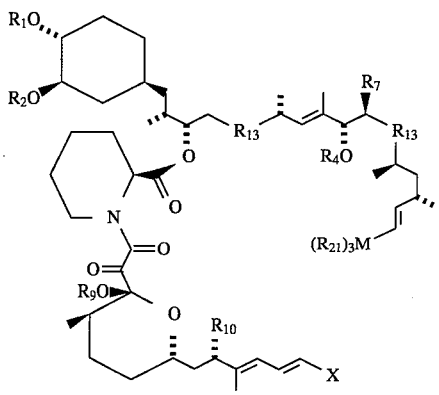

wherein $R_1$, $R_2$, $R_4$, $R_7$, $R_9$, $R_{10}$, $R_{21}$ and M are as defined above.

BRIEF DESCRIPTION OF THE DRAWINGS

The numerous objects and advantages of the present invention may be better understood by those skilled in the art by reference to the accompanying figures, in which.

DETAILED DESCRIPTION OF THE PREFERRED EMBODIMENTS

Figure 1:
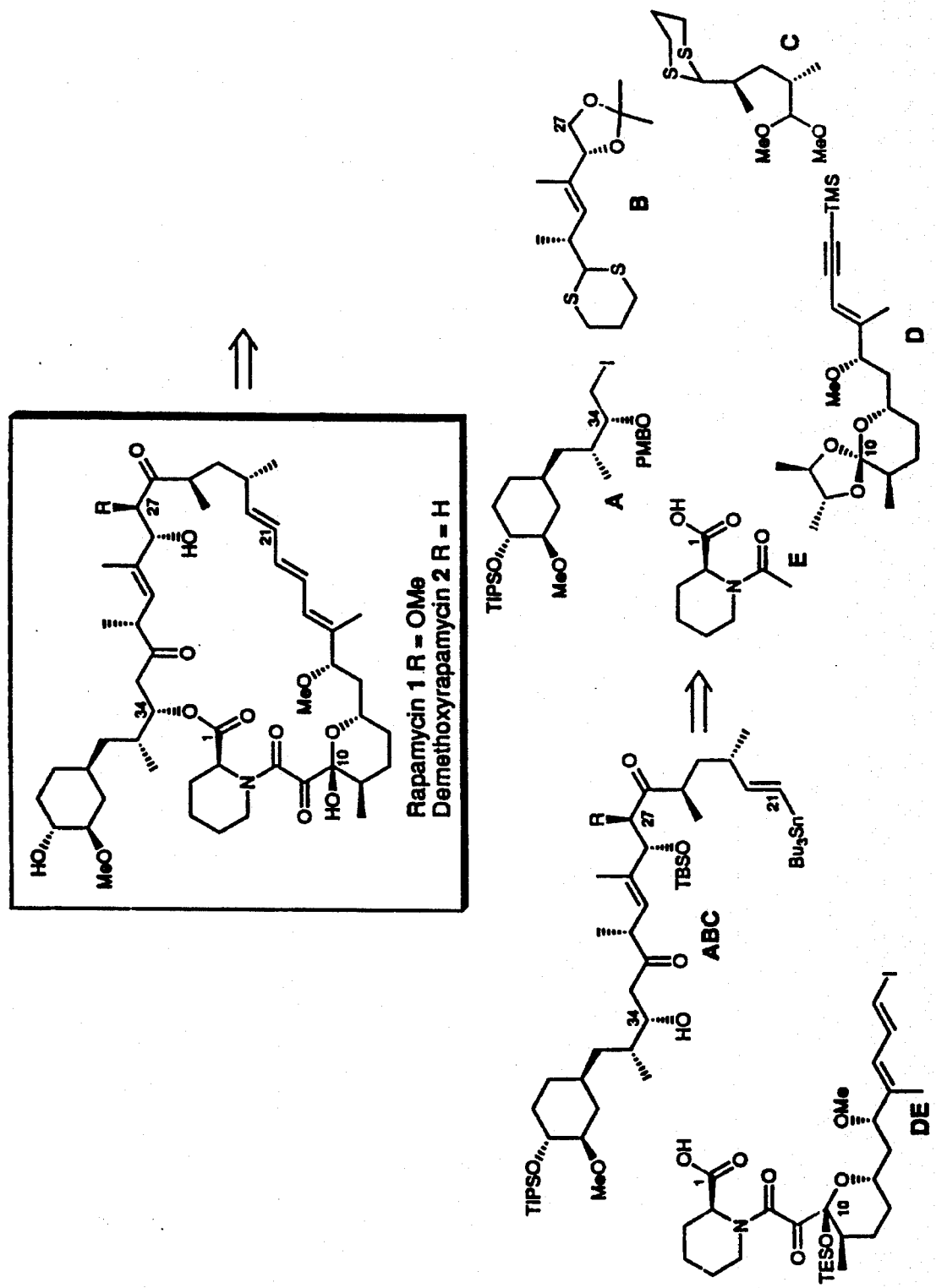
FIG. 1 shows an overview of a synthesis of the invention as applied to rapamycin and demethoxyrapamycin.

It has been found in accordance with the invention that the synthesis of macrocycles such as rapamycin and/or derivatives can be achieved by highly convergent synthetic procedures wherein fully functionalized fragments corresponding to carbons 21–34 of the rapamycin skeleton are coupled with pinecolinate-tricarbonyl fragments corresponding to carbons 1–20, each fragment being available from building blocks A through E as outlined in FIG. 1.

Figure 2:
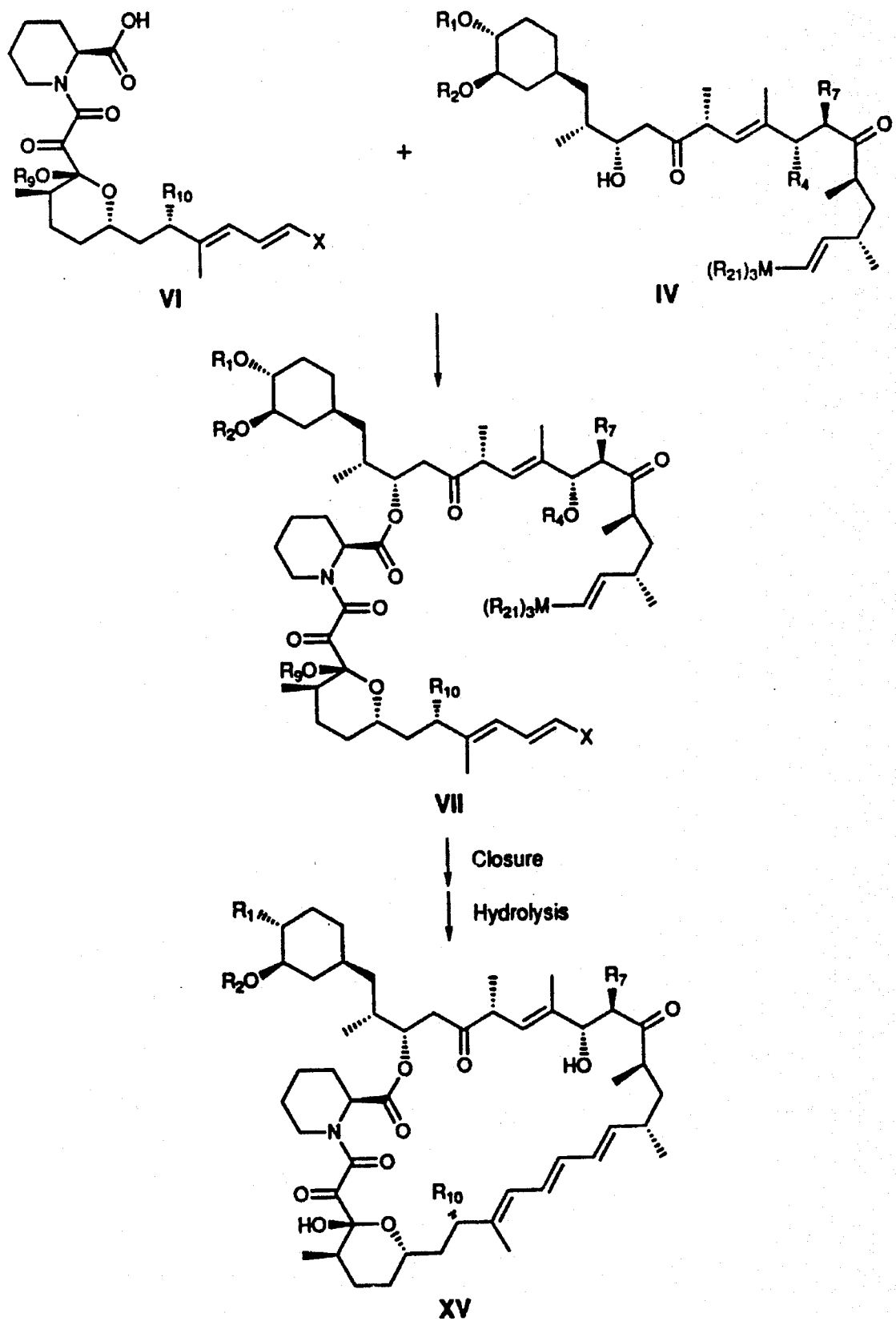
FIG. 2 shows the preparation of compounds XV and VII from compounds IV and VI.

In preferred embodiments rapamycin or demethoxyrapamycin are prepared from compound VII, which is in turn prepared from precursor fragments IV and VI according to FIG. 2. Preferably, compound IV is first coupled to compound VI by an intermolecular acylation to form compound VII. A preferred condensation agent for the acylation is ethyl-3-(3-dimethylamino)-propyl carbodiimide.HCl (EDAC.HCl), dimethylamino pyridine (DMAP). Closure of the ring in compound VII is preferably achieved by a Pd(0)-catalyzed Stille coupling. A preferred reagent for the coupling is $(2\text{-furyl}_3P)_2PdCl_2$, diisopropylethylamine (DIPEA) in DMF/THF. After ring closure, the protecting groups are preferably removed by any of several reagents known in the art to be suitable, for example tetrabutylammonium fluoride/acetic acid (TBAF/AcOH) followed by HF.pyridine, pyridine in THF.

The methods of the present invention allow flexibility in choice of substituents on the rapamycin skeleton. For example, $R_7$ can be varied to provide different rapamycin derivatives. In one preferred embodiment $R_7$ is hydrogen, and the resulting product is demethoxyrapamycin. Other similar substitutions may be made at other positions in the rapamycin skeleton, for example, at C-16.

Figure 3:
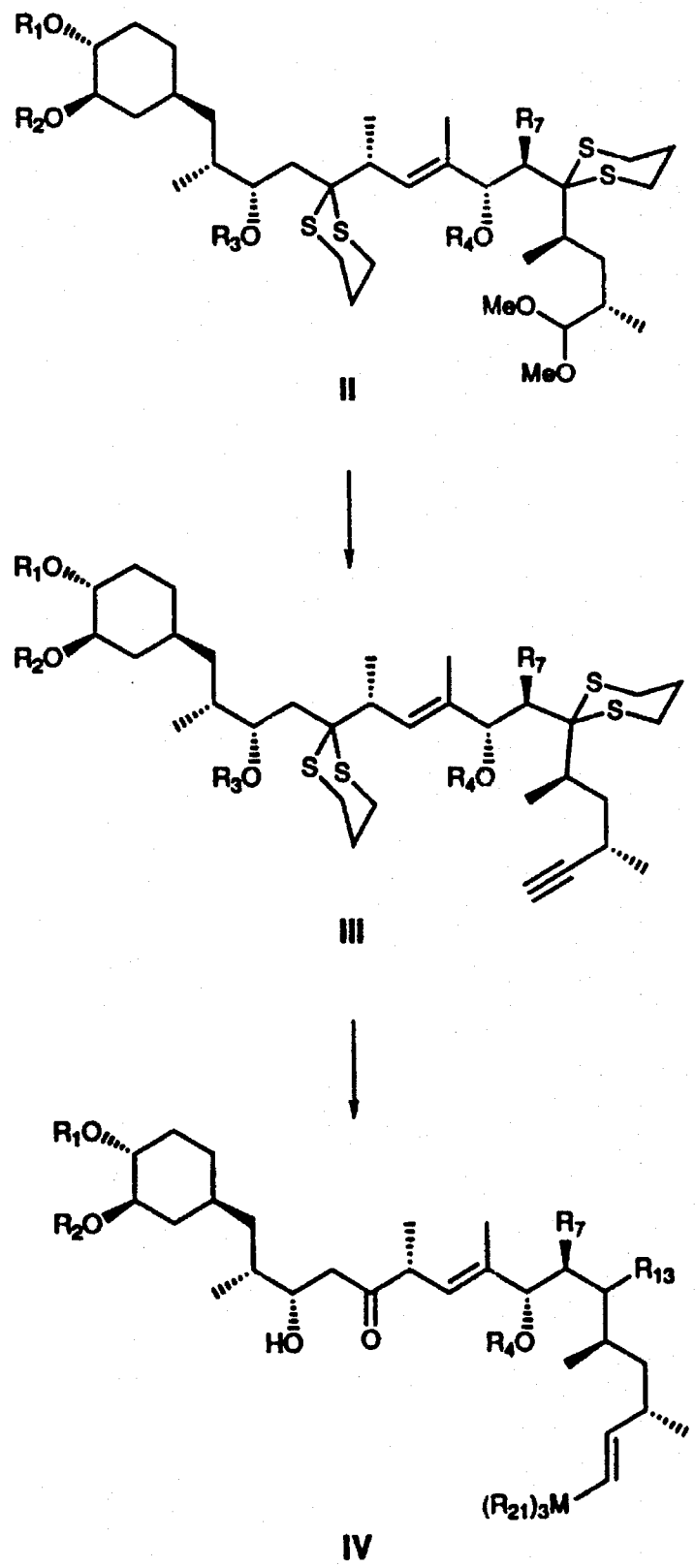
FIG. 3 shows the preparation of fragment IV from precursor compound II.

The preparation of fragment IV from common precursor compound II is shown in FIG. 3. Compound II is first treated to unmask the aldehyde group by reaction with, for example, TsOH in acetone, and then subjected to Corey-Fuchs homologation to yield the terminal acetylene compound III. See, Corey, E. J. and Fuchs, P. L., *Tetrahedron Lett.* 1972 13, 3769. Compound III is, in turn, treated to remove the protecting group at C-34. In preferred embodiments the protecting group at C-34 is PMBO (p-methoxybenzyloxy), which is preferably removed oxidatively by, for example, DDQ (2,3-dichloro-5,6-dicyano-1,4-benzoquinone) in $CH_2Cl_2$. This is followed by hydrolysis of the dithiane group with, for example, MeI, $CaCO_3$, and palladium(0)-mediated hydrostannylation. See Zhang, H. X. et al., *J. Org. Chem.* 1990 55, 1857.

Figure 4:
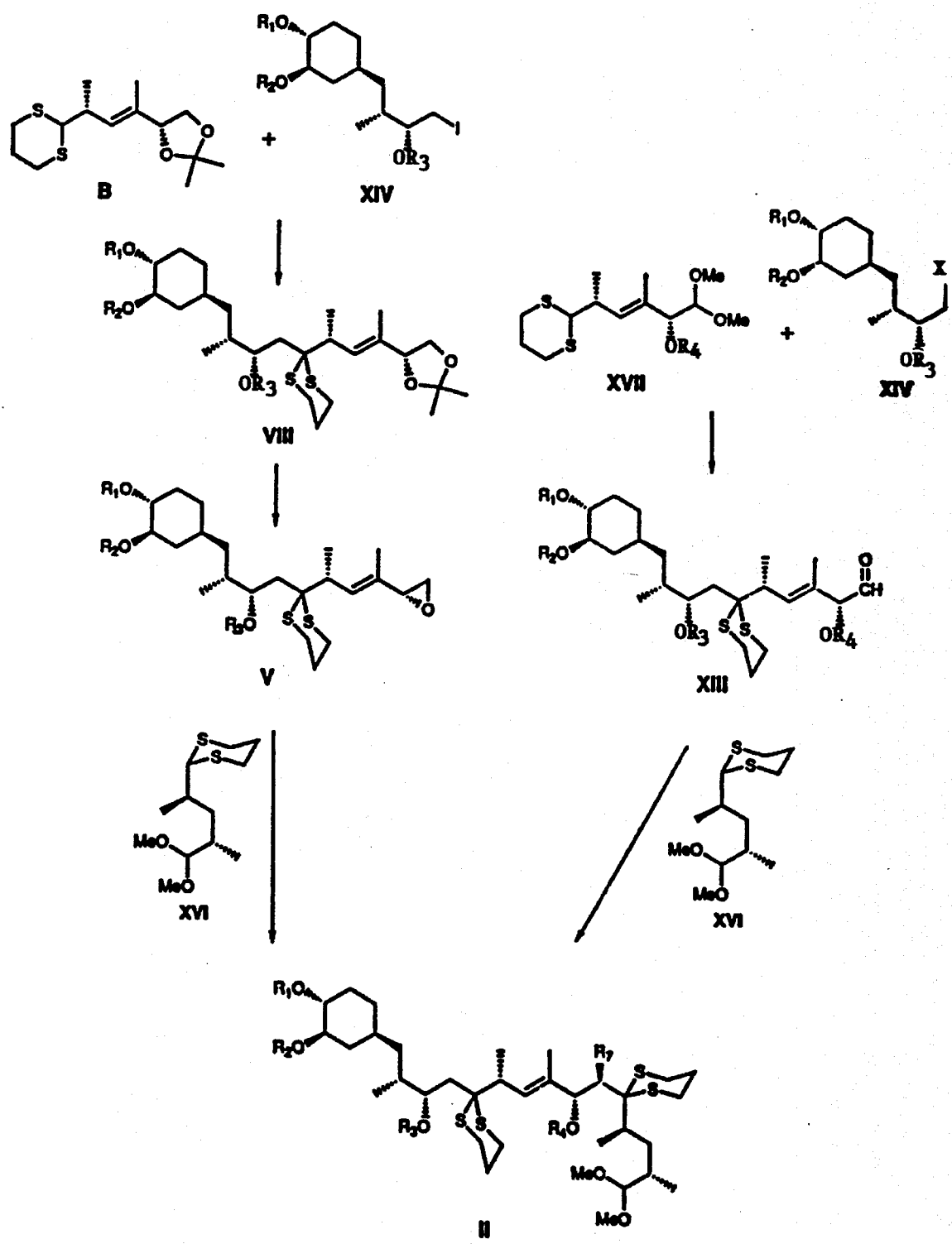
FIG. 4 shows exemplary synthetic routes for the derivation of compound II where $R_7$ is H or alkoxy.
Figure 5:
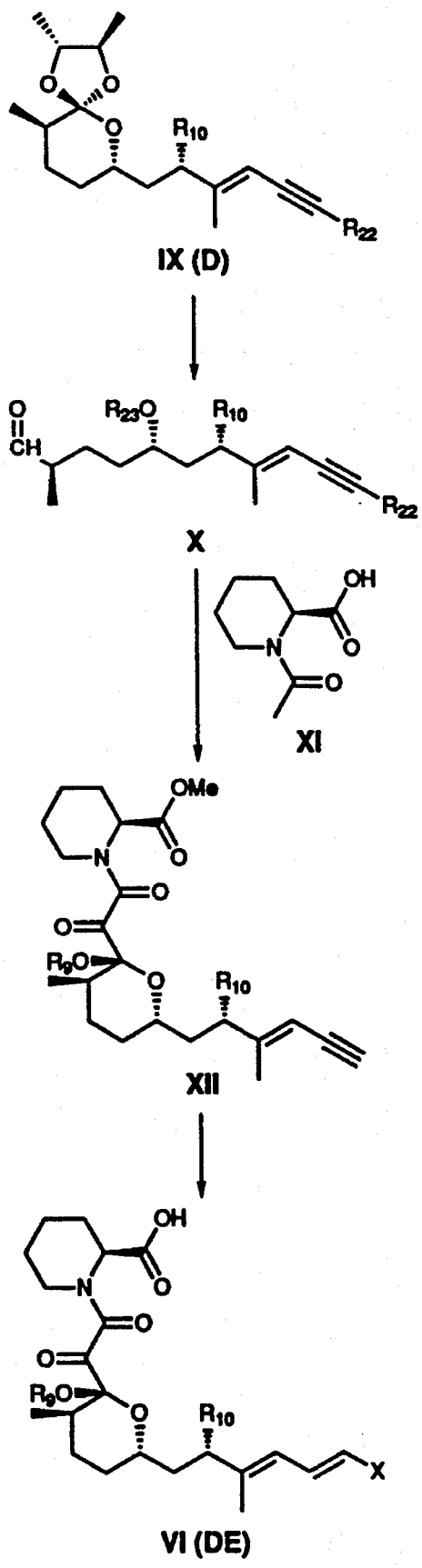
FIG. 5 shows the preparation of compound VI from fragment D.
Figure 6:
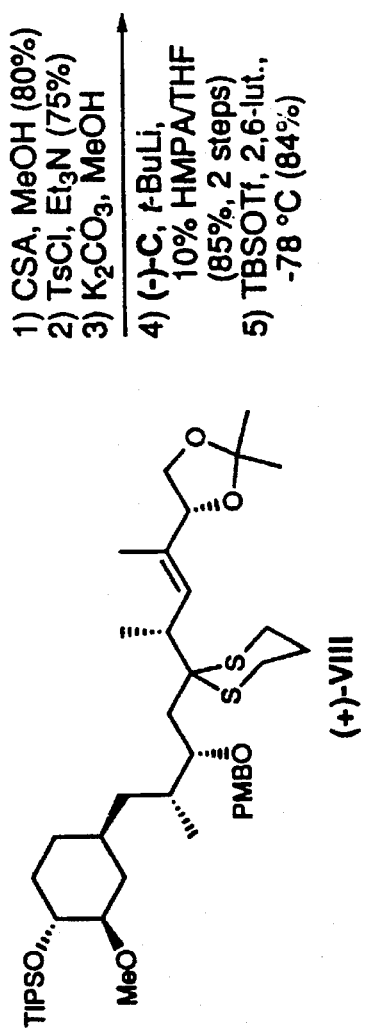
FIG. 6 shows the formation of compound II in the synthesis of demethoxyrapamycin.
Figure 6:
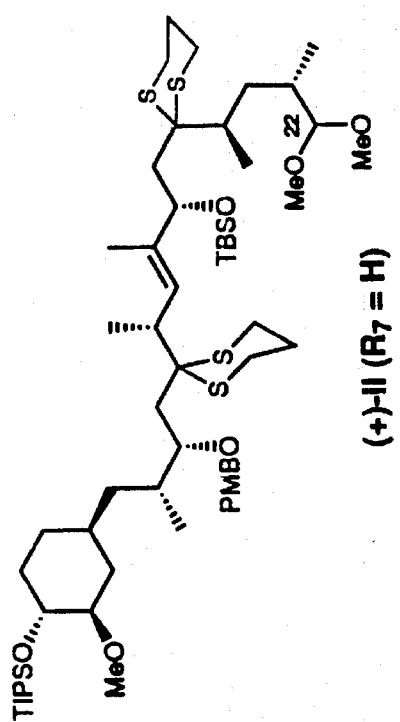
Figure 7:
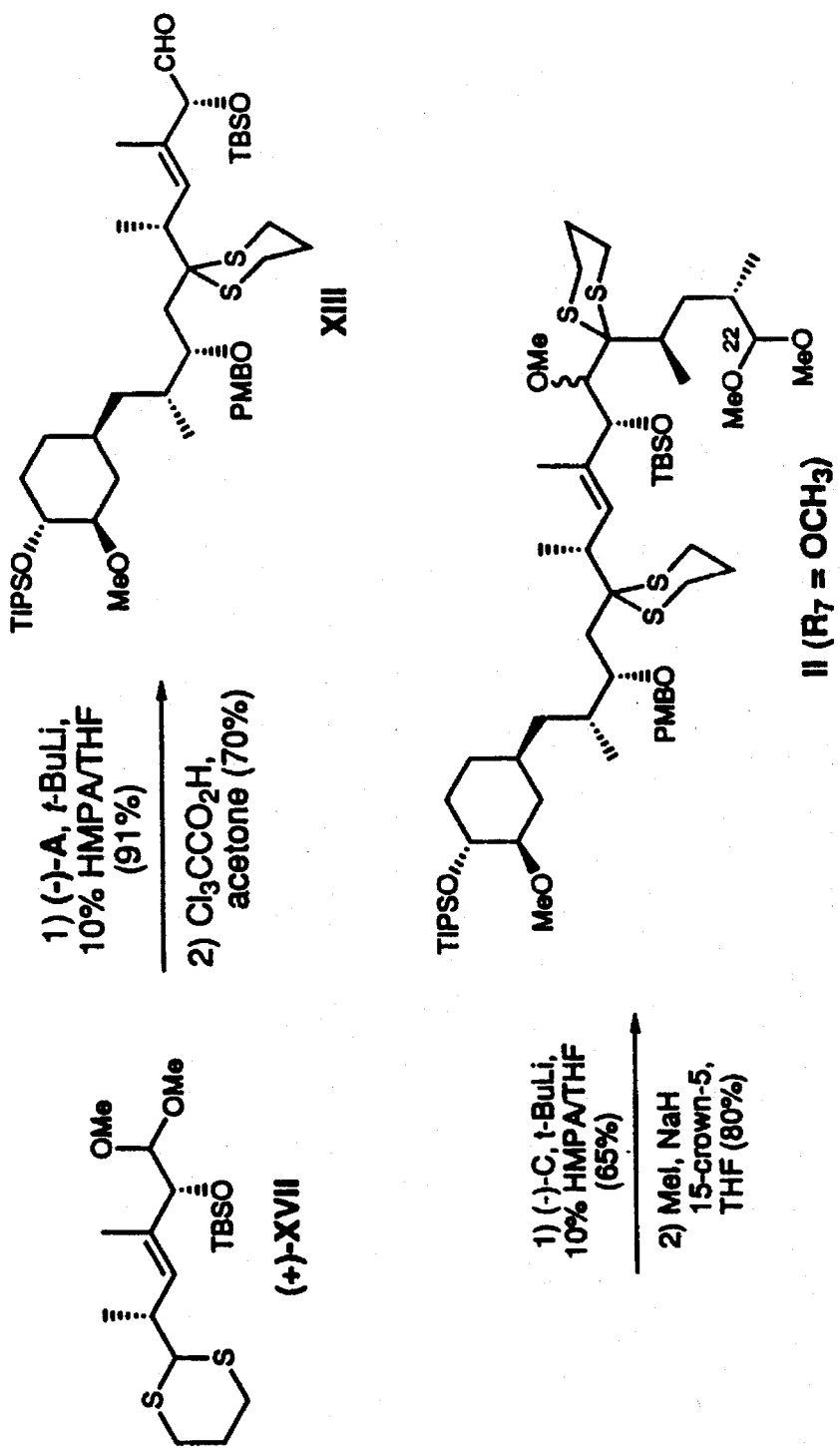
FIG. 7 shows the formation of compound II in the synthesis of rapamycin.
Figure 8:
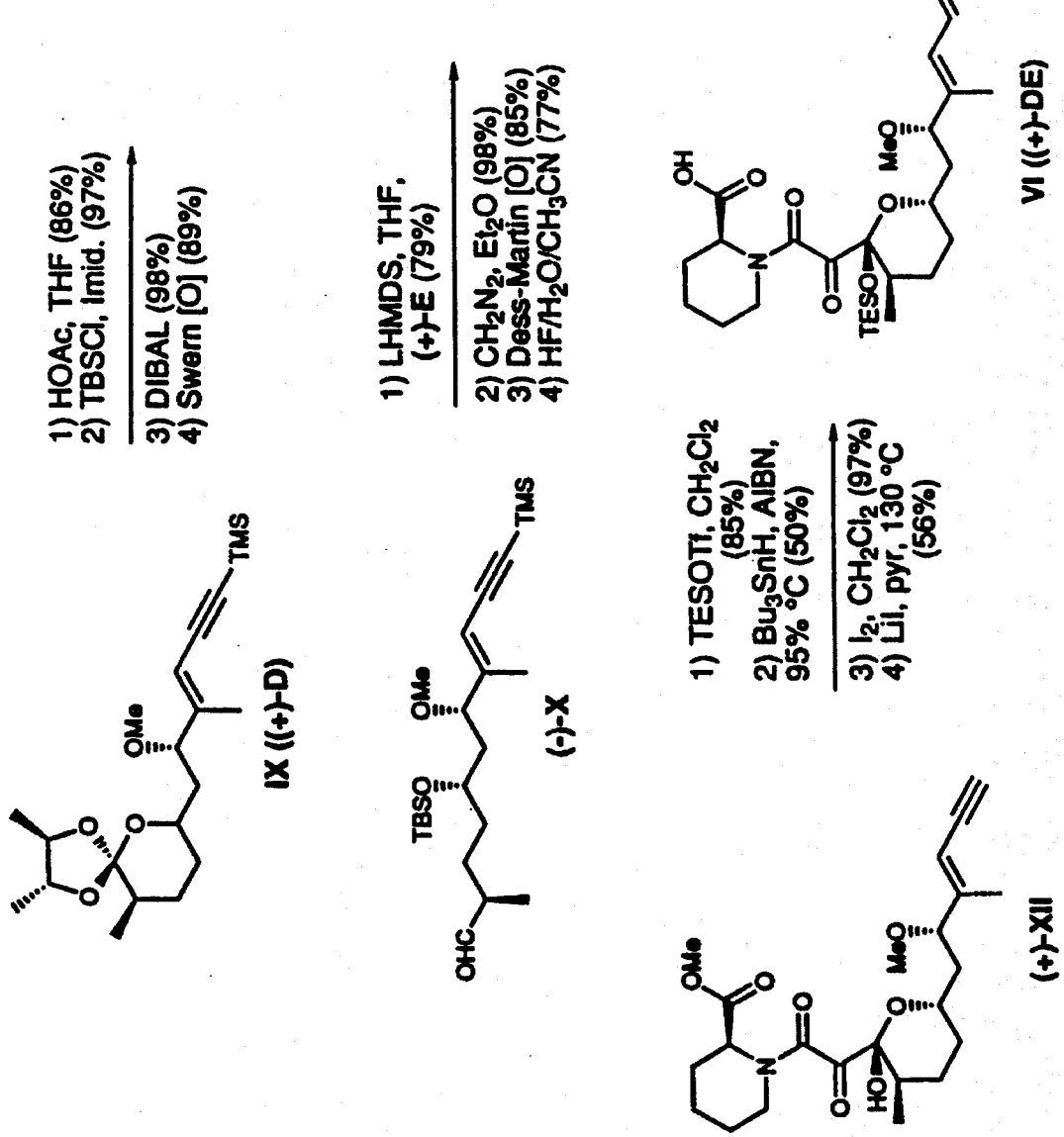
FIG. 8 shows the synthesis of compound VI (fragment DE) from fragment D.
Figure 9A:
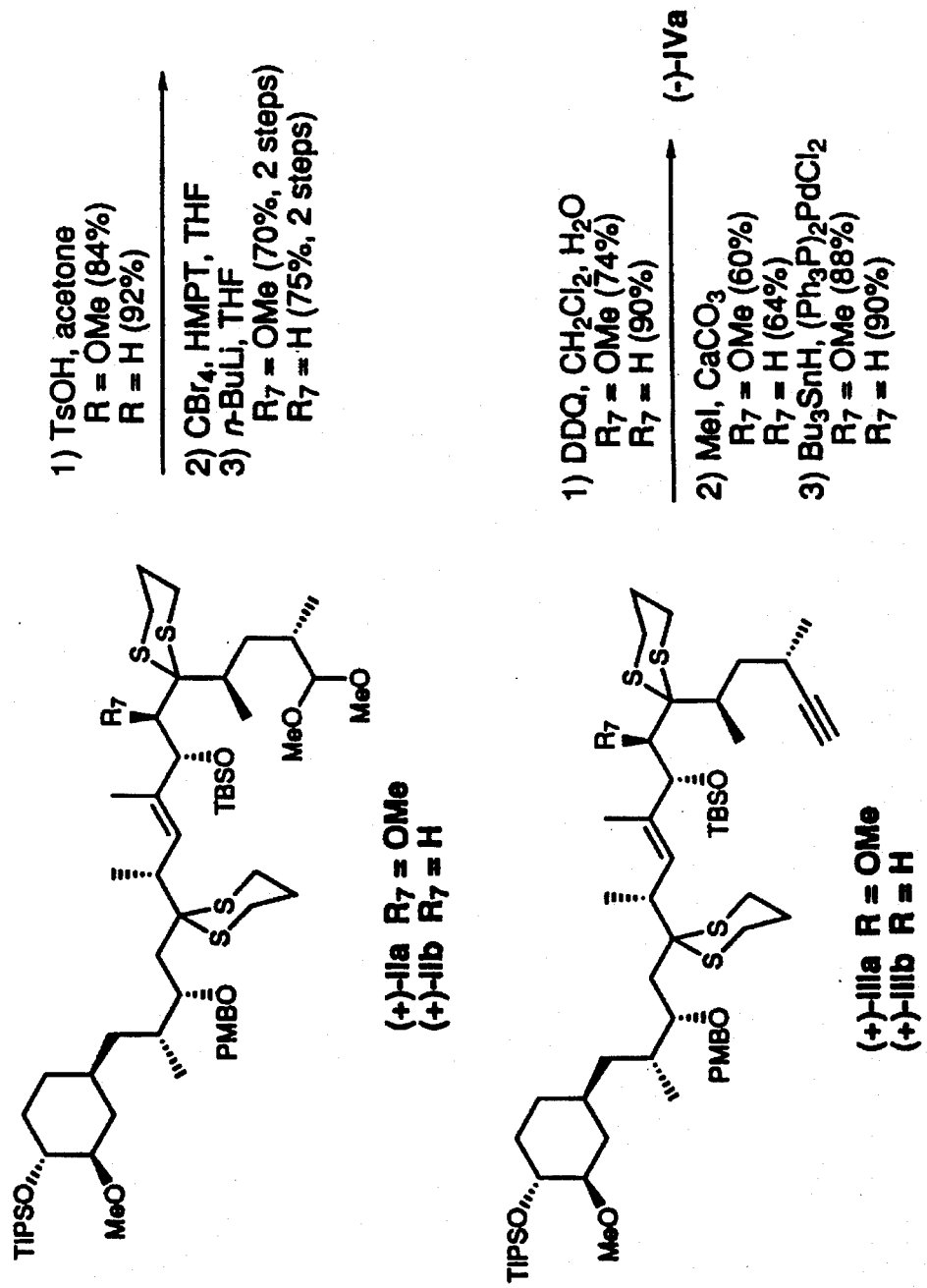
FIG. 9 shows the completion of the synthetic routes to rapamycin and demethoxyrapamycin from compounds IIa and IIb.
Figure 9B:
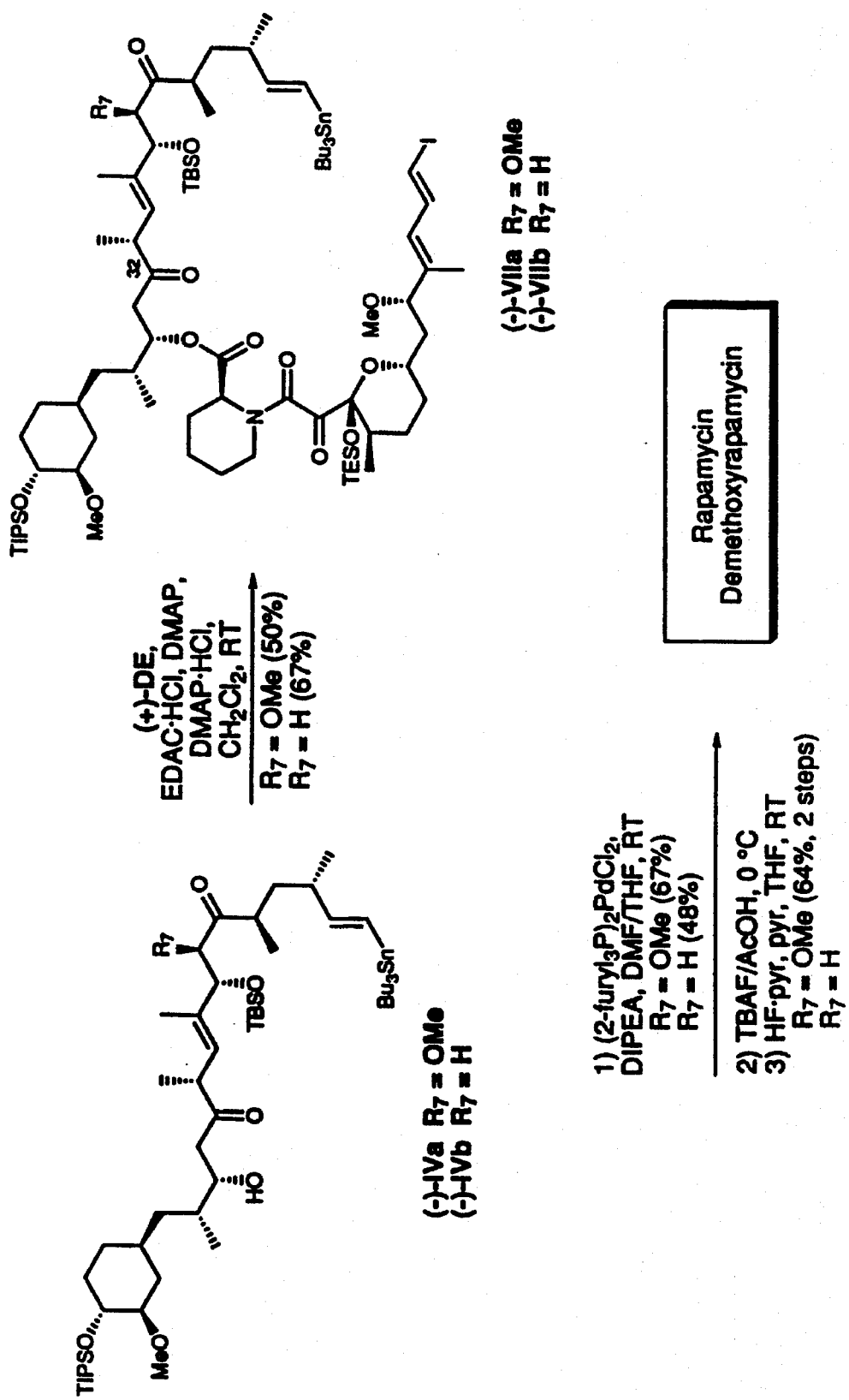

Compound II derives from two separate synthetic routes depending upon the nature of $R_7$. These synthetic routes are shown in FIG. 4. In the synthetic route leading, for example, to demethoxyrapamycin, fragment B from FIG. 1 is coupled with the butyllithium derivative of fragment A of FIG. 1 to produce precursor acetonide VIII (fragment AB). Fragments A and B can be prepared according to the procedure of Smith, A. B. et al., *Tetrahedron Letters* 1994, 35(28), 4907–4910. Epoxide V is produced from compound VIII by standard techniques, such as, for example, unmasking with camphorsulfonic acid/methanol (CSA/MeOH), tosylation, and epoxidation with $K_2CO_3$/MeOH. Compound II ($R_7$=H) is formed from the coupling of terminal epoxide V and compound XVI. Preferably, the coupling is performed at low temperature (i.e., –78° C.) using an alkyllithium reagent, for example t-BuLi, in an appropriate solvent such as, for example, 10% (v/v) HMPA (hexamethylphosphoramide)/THF. In the synthetic route leading to, for example, rapamycin, aldehyde XIII is first produced by coupling fragment A from FIG. 1 with the lithium derivative of dithiane compound XVII. Fragment C from FIG. 1, prepared according to the procedure of Smith, A. B. et al., *Tetrahedron Letters* 1994, 35(28), 4911–14 is metallated with t-butyllithium and added to aldehyde XIII, and the product is methylated to give compound II (R=OCH$_3$). The preparation of compound VI is shown in FIG. 5. Fragment D from FIG. 1, prepared according to the procedure in Smith, A. B. et al., *Tetrahedron Letters* 1994, 35(28), 4911–14, is hydrolyzed with, for example, AcOH/THF, and silated with, for example, 2 equivalents of TBSCl (t-butyldimethylsilyl chloride), imidazole, DMF. The ester is reduced by, for example DIBAL (diisobutylaluminum hydride) reduction, and aldehyde species X is formed by subsequent oxidation, for example with DMSO and oxalyl chloride by the method of Swern. See, March, J., *Advanced Organic Chemistry* Fourth Ed. Wiley & Sons New York, 1992 p. 1194.

Compound X is then condensed with the dianion of (L)-N-acetylpipecolinic acid in the presence of a condensing agent such as, for example, lithium hexamethyldisilazide (LHMDS). The products are treated with diazomethane followed by Des-Martin oxidation (5 equiv) to give the tricarbonyl species in accordance with the procedure developed by Golec, et al. See, Batchelor, M. J. et al., *Tetrahedron*

*Lett.*, 1993, 34, 167; Dees, D. B. et al., *J. Org. Chem.* 1983 48 4155. Removal of the TBS group at C-14 yields the hemiketal compound XII, which is then protected at the free hydroxyl groups by, for example, reaction with triethylsilyltrifluoromethane sulfonate (TESOTf). Compound VI (fragment DE) is then formed from compound XII by free radical hydrostannylation according to the procedure of Nicolaou, et al., *Synthesis* 1986, 453, using, for example $Bu_3SnH$, 2,2'-azobisisobutrylonitrile (AIBN), tin-iodide exchange according to the procedure of Crisp, et al., *Tetrahedron Letters* 1992, 33(32), 4649, and subsequent conversion of the ester to the carboxylic acid by, for example, LiI in pyridine.

Compounds of the invention contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Some representative protecting groups useful for protecting the for carbonyl functionality are 1,3-dithiane groups and dimethoxyacetal groups. Some representative protecting groups useful for protecting the for hydroxyl functionality are TIPS (triisopropylsilyl), PMB methoxybenzyl), TBS (t-butyldimethylsilyl), TES/triethylsilyl) and lower alkyl groups such as methyl. Other representative groups may be found in Greene, T. W. and Wuts, P. G. M., *"Protective Groups in Organic Synthesis"* 2d. Ed., Wiley & Sons, 1991. In preferred embodiments $R_1$ is TIPS, $R_3$ is PMB, $R_4$ is TBS, and $R_9$ is TES.

$R_2$ is preferably hydrogen or alkyl having from one to about six carbons. Alkyl groups according to the invention include straight chain, branched, and cyclic hydrocarbons such as methyl, isopropyl, and cyclohexyl groups. Alkoxy groups are oxygen atoms having an alkyl group appended thereto. It will be recognized that a wide variety of compounds according to the invention can readily be prepared according to the methods of the invention.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A compound of formula VII:

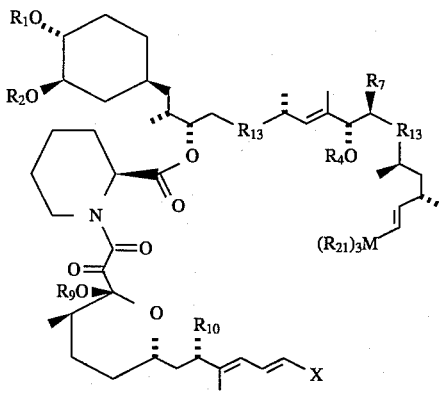

VII wherein:

$R_1$, $R_4$, and $R_9$ are, independently, hydrogen or a hydroxyl protecting group;

$R_2$ is alkyl having from one to about six carbon atoms;

$R_7$ is hydrogen or alkoxy having one to about six carbon atoms;

$R_{10}$ is H, OH, or alkoxy having one to about six carbon atoms;

$R_{13}$ is a carbonyl group or a protected derivative thereof;

$R_{21}$ is alkyl having one to about six carbon atoms;

M is a tetravalent metal atom; and

X is halogen.

2. A compound of formula:

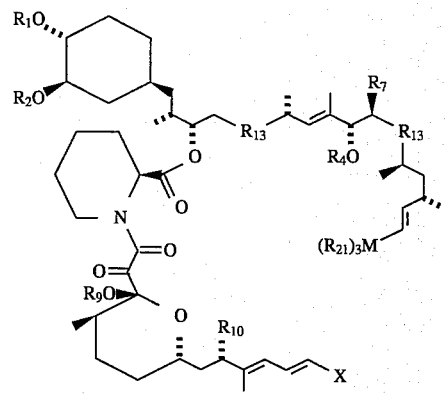

wherein:

$R_1$, $R_4$, and $R_9$ are, independently, hydrogen or a hydroxyl protecting group;

$R_2$ is alkyl having from one to about six carbon atoms;

$R_7$ is hydrogen or alkoxy having one to about six carbon atoms;

$R_{10}$ is H, OH, or alkoxy having one to about six carbon atoms;

$R_{13}$ is a carbonyl group or a protected derivative thereof;

$R_{21}$ is alkyl having one to about six carbon atoms;

M is Sn; and

X is halogen.

3. The compound of claim 1 wherein $R_7$ is H.

4. The compound of claim 1 wherein $R_7$ is methoxy.

5. The compound of claim 1 wherein said protected derivative of said carbonyl group of said group $R_{13}$ is a 1,3-dithiane.

6. The compound of claim 1 wherein $R_2$ is methyl.

7. The compound of claim 1 wherein said hydroxyl protecting groups are selected from the group consisting of TIPS, PMBO, TES and TBS.

8. The compound of claim 1 wherein $R_1$ is TIPS, $R_4$ is TBS, and $R_9$ is TES.

9. The compound of claim 1 wherein $R_{21}$ is butyl.

10. The compound of claim 1 wherein X is iodine.

* * * * *